United States Patent
Pak

(10) Patent No.: US 7,740,887 B2
(45) Date of Patent: Jun. 22, 2010

(54) CONCENTRATED BEVERAGE COMPOSITION FOR HAIR HEALTH CARE, METHOD OF MANUFACTURING THE CONCENTRATED BEVERAGE COMPOSITION AND NATURAL TEA COMPRISING THE SAME

(76) Inventor: Young Joon Pak, 4F, 290-2, Pyeongtaek-dong, Pyeongtaek-si (KR)

( * ) Notice: Subject to any disclaimer, the term of this patent is extended or adjusted under 35 U.S.C. 154(b) by 33 days.

(21) Appl. No.: 12/142,646

(22) Filed: Jun. 19, 2008

(65) Prior Publication Data

US 2009/0317351 A1 Dec. 24, 2009

(51) Int. Cl.
*A61K 36/48* (2006.01)
*A61K 36/55* (2006.01)
*A61K 36/53* (2006.01)
*A61K 36/81* (2006.01)

(52) U.S. Cl. .................. 424/757; 424/768; 424/745; 424/760

(58) Field of Classification Search .................. None
See application file for complete search history.

(56) References Cited

FOREIGN PATENT DOCUMENTS

| JP | 08127517 A | * | 5/1996 |
| JP | 10218737 A | * | 8/1998 |
| KR | 2001044451 A | * | 5/2001 |
| KR | 2003000708 A | * | 1/2003 |
| KR | 2006084931 A | * | 7/2006 |

OTHER PUBLICATIONS

Soulcysters.com. 2002 Retrieved from the internet. <http://www.Soulcysters.net/hair-loss-i-found-interesting-mainly-mention-evening-primrose-oil-11461/>. pp. 1-6. Retrieved on Jan. 27, 2010.*
Roh et al. The Hair Growth Promoting Effect of Sophora Flavescens Extract and Its Molecular Regulation. Journal of Dermatological Science. 30. 2002. pp. 43-49.*

* cited by examiner

*Primary Examiner*—Patricia Leith
*Assistant Examiner*—Melenie McCormick
(74) *Attorney, Agent, or Firm*—Marshall, Gerstein & Borun LLP

(57) ABSTRACT

Disclosed are a concentrated beverage composition for hair health care, a method of manufacturing the concentrated beverage composition, and a natural tea comprising the same. The concentrated beverage composition for hair health care comprises 100 parts by weight of water, 10 to 20 parts by weight of *Pleuropterus multiflorus* extract, 5 to 20 parts by weight of *Sophora flavescens* extract, 1 to 5 parts by weight of black bean extract, 5 to 10 parts by weight of African black sesame extract; 1 to 10 parts by weight of pomegranate extract; 5 to 10 parts by weight of *Oenothera odorata* seeds extract; and 5 to 10 parts by weight of *Sophora japonica* extract.

16 Claims, No Drawings

CONCENTRATED BEVERAGE COMPOSITION FOR HAIR HEALTH CARE, METHOD OF MANUFACTURING THE CONCENTRATED BEVERAGE COMPOSITION AND NATURAL TEA COMPRISING THE SAME

BACKGROUND OF THE INVENTION

1. Field of the Invention

The present invention relates to a beverage composition, a method of manufacturing the beverage composition, and a natural tea comprising the same, and more particularly, to a concentrated beverage composition for hair health care, a method of manufacturing the concentrated beverage composition, and a natural tea comprising the same, which may improve the health status of hair and obtain aesthetic effects.

2. Description of Related Art

In general, beverages may contain fruit juices, various additives, and the like, and can relieve people's thirst and instantaneously satisfy a variety of tastes of people using the above ingredients. Recently, as people's interest for health and beauty is increased, functional beverages having added functions such as preventing a hangover, improving blood circulation, increasing beauty and the like as well as an inherent capability of thirst relief are being focused on.

Meanwhile, people's hair may consist of a cuticle, cortex, and medulla which function to protect the human body. The importance of the hair gradually increases even in view of aesthetic aspects.

However, the people's hair may be easily damaged by external factors such as environmental pollution, and internal factors such as nutrient deficiency, excessive stress, and the like, and further cause even hair loss.

SUMMARY OF THE INVENTION

An aspect of the present invention provides a concentrated beverage composition for hair health care, a method of manufacturing the concentrated beverage composition, and a natural tea comprising the same which may improve a health status of people's hair through drinking the same.

According to an aspect of the present invention, there is provided a concentrated beverage composition for hair health care, the composition including: 100 parts by weight of water; 10 to 20 parts by weight of *Pleuropterus multiflorus* extract; 5 to 20 parts by weight of *Sophora flavescens* extract; 1 to 5 parts by weight of black bean extract; 5 to 10 parts by weight of African black sesame extract; 1 to 10 parts by weight of pomegranate extract; 5 to 10 parts by weight of *Oenothera odorata* seeds extract; and 5 to 10 parts by weight of *Sophora japonica* extract.

According to an aspect of the present invention, there is provided a method for manufacturing a concentrated beverage composition for hair health care, the method including: preparing a mixture of raw sources and water, the raw sources comprising *Pleuropterus multiflorus*, *Sophora flavescens*, black bean, African black sesame, pomegranate, *Oenothera odorata* seeds, and *Sophora japonica*; preparing an extract solution comprising *Pleuropterus multiflorus* extract, *Sophora flavescens* extract, black bean extract, African black sesame extract, pomegranate extract, *Oenothera odorata* seeds extract, and *Sophora japonica* extract using the prepared mixture; and preparing a concentrated solution by concentrating the prepared extract solution.

According to an aspect of the present invention, there is provided a natural tea for hair health care, the natural tea including: a concentrated beverage composition comprising 100 parts by weight of water, 10 to 20 parts by weight of *Pleuropterus multiflorus* extract, 5 to 20 parts by weight of *Sophora flavescens* extract, 1 to 5 parts by weight of black bean extract, 5 to 10 parts by weight of African black sesame extract, 1 to 10 parts by weight of pomegranate extract, 5 to 10 parts by weight of *Oenothera odorata* seeds extract, and 5 to 10 parts by weight of *Sophora japonica* extract; and 300 to 900 parts by weight of ion water comprising germanium, based on 100 parts by weight of the concentrated beverage composition.

DETAILED DESCRIPTION OF EXEMPLARY EMBODIMENTS

Hereinafter, a concentrated beverage composition for hair health care, a method of manufacturing the concentrated beverage composition, and a natural tea comprising the same according to the present invention will be described in detail.

The concentrated beverage composition for hair health care may be separately drunk, however the present invention is not limited thereto. As an example, the concentrated beverage composition for hair health care may be mixed with ion water comprising germanium to thereby manufacture a natural tea for drink. As another example, the concentrated beverage composition for hair health care may be added to dairy products such as milk, soy milk, yogurt, and the like by a certain amount. In addition, the concentrated beverage composition for hair health care may be added to a variety of other beverages. Herein, various additives may be added to the natural tea, the dairy products, and the variety of other beverages depending on people's preference.

The concentrated beverage composition for hair health care according to the present invention may comprise 100 parts by weight of water, 10 to 20 parts by weight of *Pleuropterus multiflorus* extract, 5 to 20 parts by weight of *Sophora flavescens* extract, 1 to 5 parts by weight of black bean extract, 5 to 10 parts by weight of African black sesame extract, 1 to 10 parts by weight of pomegranate extract, 5 to 10 parts by weight of *Oenothera odorata* seeds extract, and 5 to 10 parts by weight of *Sophora japonica* extract.

Also, the concentrated beverage composition for hair health care may further comprise 0.1 to 2 parts by weight of *Laminaria japonica* extract and 0.1 to 2 parts by weight of rosemary extract. Also, the concentrated beverage composition for hair health care may further comprise 1 to 5 parts by weight of *Arctium lappa* extract, 1 to 5 parts by weight of *Betula platyphylla* var. *japonica* extract, 0.1 to 2 parts by weight of capsicum extract, 0.1 to 2 parts by weight of hop extract, and 0.1 to 2 parts by weight of linseed extract. In addition, the concentrated beverage composition for hair health care may further comprise other additives, etc. for the purpose of improving taste and flavor of the concentrated beverage composition for hair health care.

Hereinafter, each ingredient of the concentrated beverage composition for hair health care according to the present invention will be described in detail. The natural ingredients may be subjected to a hot water extraction method under high pressure to obtain extracts of the natural ingredients, thereby acquiring function and efficacy of the natural ingredients. Accordingly, the natural ingredients will be hereinafter described in detail.

*Pleuropterus multiflorus* is a plant belonging to Dicotyledoneae Polygonales Polygonaceae having tuber roots such as sweet potatoes, whose rhizome is pushed down into the ground. A stem of *Pleuropterus multiflorus* may branch off and stretch longer having no fur. The *Pleuropterus multiflorus* has egg-shaped leaves crossing each other and having a sharp tip. The *Pleuropterus multiflorus* may function to prevent hair loss and dandruff and enable damaged hair to be healthy hair.

*Sophora flavescens* is a plant belonging to Dicotyledoneae Rosales Leguminosae which is brought up in the sunny grass, whose height is about 80 to 100 cm, and whose color is green but black when young. The *Sophora flavescens* has a straightened stem, whose leaves cross each other and has an imparipinnately compound leaf. Main ingredients of the *Sophora flavescens* may comprise alkaloids, that is, matrine, oxy-matrine, sophoranol, anagyrine, methyl cytisine, and the like. In particular, the *Sophora flavescens* may function to suppress male hormones and sterilize *Demodex folliculorum*, thereby preventing hair loss.

Black bean may function to help kidney function, enable a blocked blood vascular system to become unblocked, counteract all poisons including mineral poison, and help blood circulation.

Black sesame may have effects on chronic gastritis, neuritis, hypertension, constipation, hyperthelesia, anemia, and the like. The black sesame may comprise gamma tocopherol (a type of vitamin E) for increasing antioxidant effect, thereby having effects of anti-aging and hair loss prevention. Herein, the black sesame grown in various areas may be used. As an example, African black sesame having vitamin E and protein richer than the black sesame grown in other areas may be used.

Pomegranate may comprise about 40% carbohydrate, and about 1.5% citric acid which is an organic acid, thereby helping blood purification and blood circulation. Also, pomegranate may comprise abundant amounts of mineral ingredients performing important functions in the human body, such as calcium (Ca), potassium (K), magnesium (Mg), zinc (Zn), iron (Fe), and the like. Also, pomegranate may suppress male hormones to prevent hair loss. In addition, pomegranate may comprise vitamins such as vitamin B1, vitamin B2, vitamin C, and the like to thereby provide superior nutrients to control various functions and prevent various diseases within the human body. In particular, a granum of pomegranate comprises isoflavon, that is, phytoestrogen of about 17 mg per 1 kg, thereby having effects of normalizing physiological functions and metabolic functions of skin.

*Oenothera odorata* has one or several upright stems grown from a thick and straight root and has a height of 50 to 90 cm. Leaves of the *Oenothera odorata* crossing each other have a sharp tip and a saw tooth on their edge.

The *Oenothera odorata* seeds includes linolenic acid and a natural γ-linolenic acid, which are precursors of prostaglandin. The *Oenothera odorata* seeds promotes composition of collagen IV and VII composing Dermo-Epidermal Junction (DEJ), thereby enhancing skin elasticity. The linolenic acid and the natural γ-linolenic acid included the *Oenothera odorata* seeds may function to promote female hormones and to suppress male hormones, thereby preventing hair loss.

The *Sophora japonica* is a broadleaf tree belonging to legume, and widely distributed in Korea, Japan, China, and the like. A bark of the *Sophora japonica* is gray or dark gray-colored, and an innerbark thereof is yellow-colored and has a unique odor. Leaves of the *Sophora japonica* grow in alternation. The *Sophora japonica* has hemostatic effect, anti-hypertensive effect, and anti-inflammatory effect.

The *Laminaria japonica* comprises abundant amounts of natural vitamins to provide various nutrients to the root of hair, and function to remove the keratin of the scalp and prevent aging of the scalp, and thus preventing hair loss.

The rosemary is a type of herb and widely used, and has superior anti-aging effects. The rosemary may prevent the dandruff from being generated on the scalp, thereby preventing hair loss.

The *Arctium lappa* is a crop having a relatively high growth temperature of about 20° C. to 25° C., and winter sowing and autumn sowing of the *Arctium lappa* may be possible due to its strong resistance against the cold. The *Arctium lappa* may function to simulate metabolism and blood circulation. Also, the *Arctium lappa* may comprise vitamin B1, vitamin B2, and niacin to thereby help cell growth.

The *Betula platyphylla* var. *japonica* is a tree belonging to Betulaceae, which is grown in northern mountainous areas, and whose height reaches about 20 m. Cascara of the *Betula platyphylla* var. *japonica* is white, and stripped off in parallel, and whose young branch is red-brown having red dots. The *Betula platyphylla* var. *japonica* may have effects of suppressing creation of inflammatory mediators such as arachidonic acid, prostaglandin, leukotriene, and the like, thereby having superior abirritant effects. The cascara of the *Betula platyphylla* var. *japonica* may have effects on liver cirrhosis, have antipyretic action, and function to stop coughing.

The capsicum is spicy natural ingredients, and the spicy taste results from capsaicin ingredients. The capsaicin ingredients may promote secretion of gastric juice to thereby enhance one's appetite and promote the blood circulation. Also, the capsicum may have an effect on mucous such as diluting mucus to expel sputum to the outside of the human body, and also have analgesic effect such as temporarily paralyzing functions of neural transmission cells. As an extract of the capsicum, capsicum tincture may be given. The capsicum tincture may stimulate root of hair to thereby promote hair growth.

The hop is a vine plant of perennial plants belonging to the White Mulberry, and may be used as an ingredient of beer. The hop may comprise lupulin ingredient, which is a mixture of Humulen, Myrcene, Humulon, Lupulon, hop resin, and the like. The hop may have antimicrobial effect, sedative effect, and antiseptic effect.

The linseed is eatables cultivated in a relatively cold area and thereby a large amount of the linseeds are not produced. However, the linseed has excellent efficacy and nutrition, and includes a large amount of protein, essential fatty acids, anti-carcinogen. The linseed has various effects such as heart disease prevention, stroke prevention, coprostasis treatment, diet, brain growth and development, hormone-related disease prevention, anticancer, and the like. Also, the linseed has excellent effects on skin diseases occurring due to chloasma, freckles, ultraviolet light, and the like, and prevents atopic skin diseases.

Extracts extracted from the above-described natural ingredients may have each function and efficacy of the respective natural ingredients. Accordingly, the concentrated beverage composition for hair health care according to the present invention including the above extracts may improve the health status of hair to thereby obtain aesthetic effects.

Hereinafter, a method for manufacturing the concentrated beverage composition for hair health care according to the present invention will be described in detail.

The method for manufacturing the concentrated beverage composition for hair health care according to the present invention may comprise preparing a mixture of raw sources and water, the raw sources comprising *Pleuropterus multiflorus, Sophora flavescens,* black bean, African black sesame, pomegranate, *Oenothera odorata* seeds, and *Sophora japonica*, preparing an extract solution comprising *Pleuropterus multiflorus* extract, *Sophora flavescens* extract, black bean extract, African black sesame extract, pomegranate extract, *Oenothera odorata* extract seeds, and *Sophora japonica* extract using the prepared mixture, and preparing a concentrated solution by concentrating the prepared extract solution.

Herein, the raw sources may further comprise *Laminaria japonica*, and rosemary. As a result, the extract solution and concentrated solution may further comprise *Laminaria japonica* extract, rosemary extract. Also, the raw sources may further comprise *Arctium lappa*, *Betula platyphylla* var. *japonica*, capsicum, hop, and the linseed. As a result, the extract solution and concentrated solution may further comprise *Arctium lappa* extract, *Betula platyphylla* var. *japonica* extract, capsicum extract, hop extract, and linseed extract.

First, the preparing of the mixture will be herein described in detail. For example, the raw sources are cleaned by washing, and the washed raw sources are put into a flexible pouch. Next, water of 1 to 20 times the amount relative to the raw sources at about 20° C. to about 50° C. is added in the pouch, and then the pouch is sealed, thereby preparing the mixture.

Next, the preparing of the extract solution may include pressing the prepared mixture and filtering the mixture. As an example, the pouch is pressed with about 100 to about 600 MPa pressure at about 80° C. to about 100° C. for about 30 to about 300 minutes. In these processes, the raw sources are subjected to a hot water extraction to obtain each of the extracts. Next, the raw sources, not being subjected to the hot water extraction, from among the mixture may be filtered. Herein, a typical hot water extraction scheme instead of the above-described hot water extraction scheme using high pressure may be used, and also other various schemes may be used.

Next, the preparing of the concentrated solution may prepare the concentrated solution such that the weight of the concentrated solution is about 5% to about 20% of the weight of the extract solution. As an example, the prepared extract solution is heated to about 80° C. to about 100° C. for about 30 to about 200 minutes, thereby controlling the weight of the concentrated solution. The concentrated solution prepared after the above-described process is performed may comprise extracts of the raw sources and water, and each content of the extracts is the same as the above.

As described above, the concentrated beverage composition for hair health care according to the present invention may be manufactured by the preparing of the mixture, the preparing of the extraction solution using the mixture, and the preparing of the concentrated solution using the extraction solution. The concentrated beverage composition for hair health care according to the present invention may improve the health status of hair to thereby obtain beauty effects.

A natural tea for hair health care according to the present invention will be hereinafter described in detail.

The natural tea for hair health care according to the present invention may comprise a concentrated beverage composition comprising 100 parts by weight of water, 10 to 20 parts by weight of *Pleuropterus multiflorus* extract, 5 to 20 parts by weight of *Sophora flavescens* extract, 1 to 5 parts by weight of black bean extract, 5 to 10 parts by weight of African black sesame extract, 1 to 10 parts by weight of pomegranate extract, 5 to 10 parts by weight of *Oenothera odorata* seeds extract, and 5 to 10 parts by weight of *Sophora japonica* extract, and 300 to 900 parts by weight of ion water comprising germanium, based on 100 parts by weight of the concentrated beverage composition.

Herein, the concentrated beverage composition according to the present invention may further comprise 0.1 to 2 parts by weight of *Laminaria japonica* extract, and 0.1 to 2 parts by weight of rosemary extract, based on 100 parts by weight of ion water of the concentrated beverage composition. Also, the concentrated beverage composition according to the present invention may further comprise 1 to 5 parts by weight of *Arctium lappa* extract, 1 to 5 parts by weight of *Betula platyphylla* var. *japonica* extract, 0.1 to 2 parts by weight of capsicum extract, 0.1 to 2 parts by weight of hop extract, and 0.1 to 2 parts by weight of linseed extract, based on 100 parts by weight of ion water of the concentrated beverage composition.

The natural tea may comprise ingredients other than the above-described ingredients depending on people's preference. As an example, ingredients having a sour taste such as a lemon juice and a sweet taste such as sugar may be further added in the natural tea.

The ion water comprising germanium may have efficacy of the germanium. Specifically, the germanium may supplement oxygen to the human body to have antioxidant action, thereby preventing acidification of blood in the human body, and preventing aging of cells. Also, the germanium may combine with wastes within the blood vessel, such as cholesterol, lipid, thrombus, and the like to thereby cleanse the blood, improve circulation of the blood, and control blood pressure. As a result, the germanium may combine with various heavy metals such as mercury (Hg), cadmium (Cd), lead (Pb), and the like, so that the combined heavy metals can be expelled to the outside of the human body. Also, the germanium may have superior antiviral action and analgesic action, and promote absorption of minerals such as calcium (Ca), zinc (Zn), and the like, thereby improving osteoporosis. Accordingly, by drinking the natural tea for hair health care, overall improvement of health status due to the germanium as well as improvement of the health status of hair may be expected.

The ion water comprising the germanium may further comprise other ingredients other than the germanium. As an example, the ion water comprising the germanium may comprise at least one from a group consisting of potassium (K), silica, sodium (Na), calcium (Ca), chlorine (Cl), carbonic acid, fluorine (F) in very small amounts. Besides, the ion water comprising the germanium may further comprise other ingredients comprised of general ion water.

Hereinafter, the present invention will be described in detail by examples. It is to be understood, however, that these examples are for illustrative purpose only, and are not construed to limit the scope of the present invention.

EXAMPLES

Example 1

Manufacturing of a Concentrated Beverage Composition for Hair Health Care 1 kg of *Pleuropterus multiflorus*, 500 g of *Sophora flavescens*, 200 g of black bean, 500 g of African black sesame, 100 g of pomegranate, 450 g of *Oenothera odorata* seeds, and 480 g of *Sophora japonica* extract were cleaned by washing, and then put into a pouch. Next, 6 kg of water at 25° C. was added in the pouch, and the pouch was sealed, thereby preparing a mixture.

Next, the pouch was pressed with about 500 MPa pressure at about 90° C. for about 100 minutes, and then *Pleuropterus multiflorus* extract, *Sophora flavescens* extract, black bean extract, African black sesame extract, and pomegranate extract were subjected to a hot water extraction. Next, raw sources not being subjected to the hot water extraction from among the mixture were filtered, thereby preparing 6.5 kg of an extraction solution.

Next, the prepared extraction solution was heated to about 95° C. for about 120 minutes, thereby preparing 560 g of a concentrated solution.

Example 2

Manufacturing of a Natural Tea for Hair Health Care 560 g of the prepared concentrated solution was added in 4 kg of ion water comprising germanium, and then 60 g of a sugar and 100 g of lemon juice were added in the ion water, thereby manufacturing the natural tea for hair health care.

Estimation of Hair Status

After 50 adults having a relatively bad hair health status drank the manufactured natural tea two times a day for one month, a sensory test with respect to change in the hair health status was carried out, and the results of the sensory test are shown in the following Table 1.

TABLE 1

|  | Very good | Good | Medial | No change |
|---|---|---|---|---|
| Change in gloss of hair | 15 | 26 | 7 | 2 |
| Hair protection | 10 | 32 | 5 | 3 |
| Reduction in itching in hair | 17 | 21 | 8 | 4 |
| Reduction in hair loss | 14 | 14 | 21 | 1 |
| Increase in hair thickness and richness | 18 | 23 | 7 | 2 |

As can be seen in Table 1, the natural tea for hair health care had effects of improving the hair health status such as gloss of hair, hair protection, itching, the hair loss, hair thickness and richness, and the like.

As described above, according to the present invention, the concentrated beverage composition for hair health care comprising extracts extracted from natural sources such as *Pleuropterus multiflorus, Sophora flavescens*, black bean, African black sesame, pomegranate, *Oenothera odorata* seeds, and *Sophora japonica* may be drunk alone, or a natural tea manufactured using the concentrated beverage composition may be drunk, thereby improving the health status of hair and obtaining beauty effects.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A concentrated beverage composition for hair health care, the composition comprising:
    100 parts by weight of water;
    10 to 20 parts by weight of *Pleuropterus multiflorus* water extract;
    5 to 20 parts by weight of *Sophora flavescens* water extract;
    1 to 5 parts by weight of black bean water extract;
    5 to 10 parts by weight of African black sesame water extract;
    1 to 10 parts by weight of pomegranate water extract;
    5 to 10 parts by weight of *Oenothera odorata* seeds water extract; and
    5 to 10 parts by weight of *Sophora japonica* water extract.

2. The composition of claim 1, further comprising:
    0.1 to 2 parts by weight of *Laminaria japonica* water extract; and
    0.1 to 2 parts by weight of rosemary water extract.

3. The composition of claim 2, further comprising:
    1 to 5 parts by weight of *Arctium lappa* water extract;
    1 to 5 parts by weight of *Betula platyphylla* var. *japonica* water extract;
    0.1 to 2 parts by weight of *Capsicum* water extract;
    0.1 to 2 parts by weight of hop water extract; and
    0.1 to 2 parts by weight of linseed water extract.

4. A method for manufacturing a concentrated beverage composition for hair health care, the method comprising:
    preparing a mixture of raw sources and water, the raw sources comprising *Pleuropterus multiflorus, Sophora flavescens*, black bean, African black sesame, pomegranate, *Oenothera odorata* seeds, and *Sophora japonica*;
    preparing an extract solution comprising *Pleuropterus multiflorus* extract, *Sophora flavescens* extract, black bean extract, African black sesame extract, pomegranate extract, *Oenothera odorata* seeds extract, and *Sophora japonica* extract using the prepared mixture; and
    preparing a concentrated solution by concentrating the prepared extract solution.

5. The method of claim 4, wherein the raw sources further comprise *Laminaria japonica*, and rosemary, and the extract solution further comprises *Laminaria japonica* extract, and rosemary extract.

6. The method of claim 5, wherein the raw sources further comprise *Arctium lappa, Betula platyphylla* var. *japonica, Capsicum*, hop, and linseed, and the extract solution further comprises *Arctium lappa* extract, *Betula platyphylla* var. *japonica* extract, *capsicum* extract, hop extract, and linseed extract.

7. The method of claim 4, wherein the preparing of the extract solution further comprises:
    pressing the prepared mixture at a pressure of about 100 to about 600 MPa for about 30 to about 300 minutes at about 80 to about 100° C.; and
    filtering the mixture.

8. The method of claim 4, wherein the preparing of the concentrated solution prepares the concentrated solution such that the weight of the concentrated solution is about 5% to about 20% of the weight of the extract solution.

9. The method of claim 4, wherein the preparing of the concentrated solution comprises heating the prepared extract solution for about 30 to about 200 minutes at about 80 to about 100° C.

10. A composition for hair health care, the composition comprising:
    a concentrated beverage composition comprising 100 parts by weight of water, 10 to 20 parts by weight of *Pleuropterus multiflorus* water extract, 5 to 20 parts by weight of *Sophora flavescens* water extract, 1 to 5 parts by weight of black bean water extract, 5 to 10 parts by weight of African black sesame water extract, 1 to 10 parts by weight of pomegranate water extract, 5 to 10 parts by weight of *Oenothera odorata* seeds water extract, and 5 to 10 parts by weight of *Sophora japonica* water extract; and 300 to 900 parts by weight of ion water comprising germanium, based on 100 parts by weight of the concentrated beverage composition.

11. The composition of claim 10, wherein the concentrated beverage composition further comprises 0.1 to 2 parts by weight of *Laminaria japonica* water extract, and 0.1 to 2 parts by weight of rosemary water extract, based on 100 parts by weight of ion water of the concentrated beverage composition.

12. The composition of claim 11, wherein the concentrated beverage composition further comprises 1 to 5 parts by weight of *Arctium lappa* water extract, 1 to 5 parts by weight of *Betula platyphylla* var. *japonica* water extract, 0.1 to 2 parts by weight of *Capsicum* water extract, 0.1 to 2 parts by weight of hop water extract, and 0.1 to 2 parts by weight of linseed water extract, based on 100 parts by weight of ion water of the concentrated beverage composition.

13. A method of improving hair health in a subject comprising the subject drinking the composition of claim 1.

14. A method of improving hair health in a subject comprising adding the composition of claim 1 to water containing germanium to form a beverage, and the subject drinking the beverage.

15. The method of claim 14, wherein the water is ion water.

16. A method of improving hair health in a subject comprising adding the composition of claim 1 to a dairy product selected from the group consisting of milk, soy milk, yogurt and a mixture thereof to form a beverage, and the subject drinking the beverage.

* * * * *